United States Patent [19]

Herrera et al.

[11] Patent Number: 5,247,185
[45] Date of Patent: Sep. 21, 1993

[54] REGULATED INFRARED SOURCE

[75] Inventors: Roger O. Herrera; James R. Braig, both of Oakland, Calif.; Daniel S. Goldberger, Boulder, Colo.

[73] Assignee: Critikon, Inc., Tampa, Fla.

[21] Appl. No.: 782,990

[22] Filed: Oct. 28, 1991

[51] Int. Cl.⁵ .............................................. G01J 1/00
[52] U.S. Cl. .............................. 250/504 R; 250/493.1; 250/495.1; 219/497
[58] Field of Search ............. 250/504 R, 495.1, 494.1, 250/493.1; 219/505, 497

[56] References Cited

U.S. PATENT DOCUMENTS

| | | | |
|---|---|---|---|
| 3,138,697 | 6/1964 | Banca et al. | 250/504 R |
| 3,205,343 | 9/1965 | DeBell et al. | 250/504 R |
| 3,309,881 | 3/1967 | Beerman | 250/493.1 |
| 3,394,257 | 7/1968 | Moldenhauer | 250/504 R |
| 3,394,259 | 7/1968 | Brown et al. | 250/504 R |
| 3,487,216 | 12/1969 | Webb | 250/504 R |
| 3,694,624 | 9/1972 | Buchta | 250/495.1 |
| 3,949,231 | 4/1976 | Blunck et al. | 250/493.1 |
| 4,103,174 | 7/1978 | McClatchie et al. | 250/493.1 |
| 4,378,489 | 3/1983 | Chabinsky et al. | 250/493.1 |
| 4,499,382 | 1/1985 | Vincent | 250/493.1 |
| 4,620,104 | 10/1986 | Nordal et al. | 250/493.1 |
| 4,644,141 | 2/1987 | Hagen et al. | 250/493.1 |
| 4,935,633 | 6/1990 | Curbelo et al. | 250/504 R |

Primary Examiner—Jack I. Berman
Assistant Examiner—Kiet T. Nguyen
Attorney, Agent, or Firm—Woodcock Washburn Kurtz Mackiewicz & Norris

[57] ABSTRACT

An infrared source which provides a miniature, highly stable and efficient source of infrared energy for use with infrared detectors and the like. The infrared source of the invention incorporates a platinum resistance temperature detector (RTD) which is integrated with the heater element to provide a means of electronic servo control of the heater temperature. The heater element and the RTD are tightly coupled thermally to provide accurate, continuous tracking and control of the heater temperature. The infrared source design provides excellent infrared energy output with less than one watt input power to the heater.

11 Claims, 3 Drawing Sheets

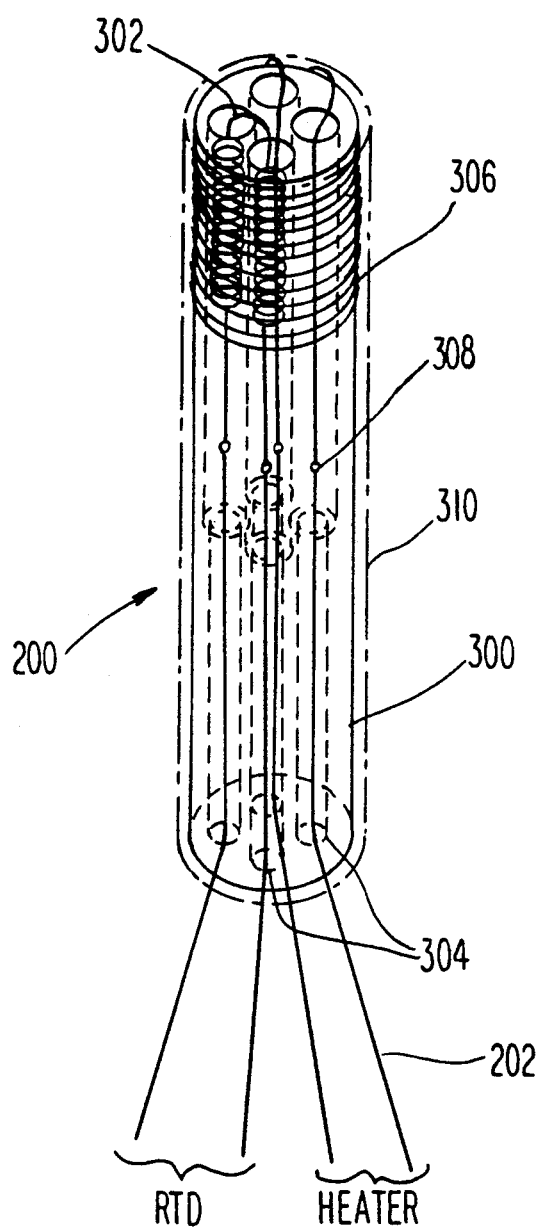
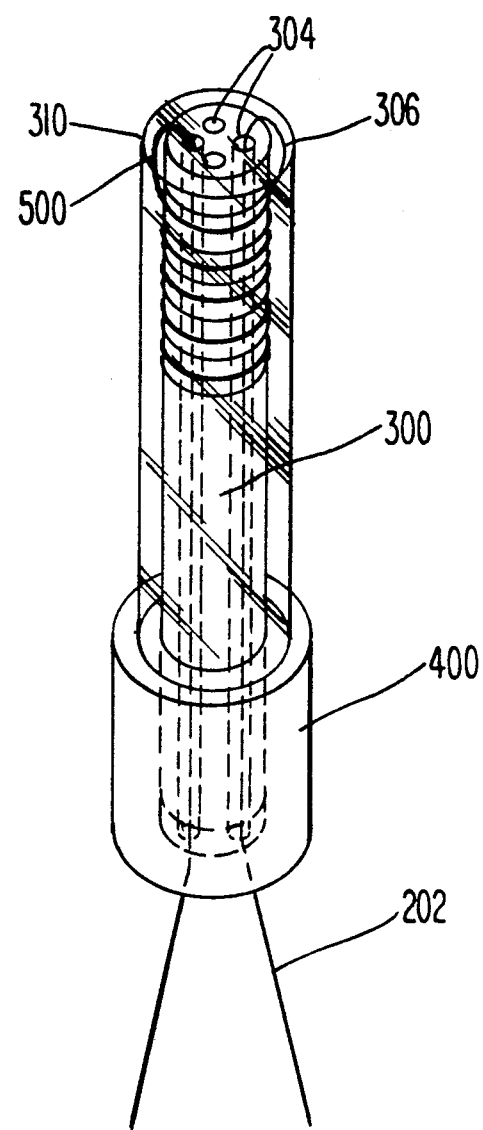
Fig. 3
Fig. 5

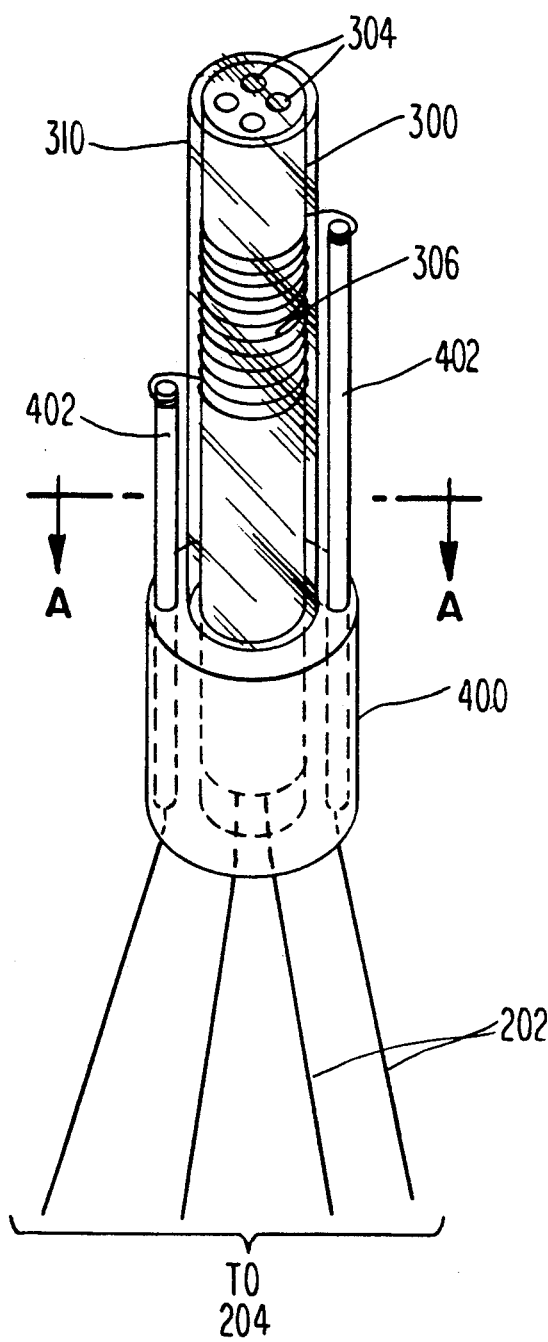
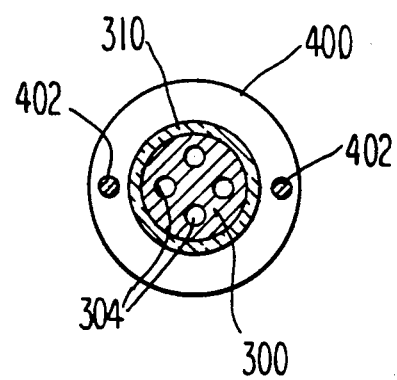
Fig. 4(b)
Fig. 4(a)

ns of the afo
REGULATED INFRARED SOURCE

BACKGROUND OF THE INVENTION

1. Field of the Invention

The present invention relates to a regulated infrared source, and more particularly, to an infrared source which has a temperature detector and feedback mechanism for maintaining the output of the infrared source at a substantially constant energy density.

2. Description of the Prior Art

Infrared energy is commonly used in detection devices for measuring desired parameters. For example, the infrared energy emitted by a target can be measured to determine the absolute temperature of that target. Thus, the infrared energy emitted by a patient can be measured by a device such as an infrared tympanic thermometer and used to determine the patient's body temperature, as described by some of the present inventors in U.S. patent application Ser. No. 07/570,205. In addition, the differential absorption effects of certain constituents at infrared wavelengths make it possible to determine the constituents of materials such as respiratory gases using an infrared capnograph detection system of the type described, for example, by some of the present inventors in U.S. patent application Ser. Nos. 07/522,177 and 07/522,208. As described therein, infrared light at wavelengths readily absorbed by a particular constituent of a patient's expired air may be passed through the patient's expired air and the degree of absorption measured to determine whether and to what extent that particular constituent is present in the expired air.

Infrared capnograph detection systems of the type described in the aforementioned patent applications operate most efficiently when the infrared source is stable and efficient yet small, lightweight and safe. Although infrared sources (otherwise known as black body radiation sources) have been generally available in the art for quite some time, suitable infrared sources have been unavailable for detecting devices which require a high degree of source stability when there are wide variations in ambient temperature, as during clinical use. Typical prior art black body radiation sources are described, for example, by M. C. Banca et al. in U.S. Pat. No. 3,138,697 and by A. G. De Bell et al. in U.S. Pat. No. 3,205,343. As described in these patents, infrared sources have been designed which operate at temperatures up to 2000° C. or even 2500° C.; however, source stability was not critical to such systems.

Other, more stable, infrared sources have been designed for use in spectrometers and the like for use in infrared spectral analysis. Such infrared sources are described, for example, in U.S. Pat. Nos. 4,499,382 to Vincent; 4,620,104 to Nordal et al.; 4,644,141 to Hagen et al. and 4,935,633 to Curbelo et al. However, these infrared sources also are not sufficiently stable for use in infrared detection devices of the type described in the aforementioned patent applications in that they frequently must be recalibrated.

The energy outputs of prior art infrared sources have been kept relatively constant in a variety of different ways. For example, Curbelo et al. teach that if the source is configured to have a small surface area radiating element which is energized by a high frequency AC square wave, where the frequency of the AC square wave is preferably much greater than the inverse of the heater filament's thermal time constant, then the infrared source's output may be kept relatively constant. However, infrared sources of the prior art remain susceptible to ambient temperature variations which cause temperature drift and subsequent drifts in the emission spectra of the infrared sources as shown in FIG. 1 for the case of a black body radiator used in an infrared gas analyzer. Unfortunately, such temperature drift is unacceptable in infrared capnograph detecting systems of the type described in the aforementioned patent applications. Accordingly, an infrared source which can maintain its output constant for a long period of time without recalibration is highly desirable.

Other techniques are known in the art for stabilizing infrared sources against ambient temperature variations. For example, the infrared source may be placed in an environment maintained at a substantially constant ambient temperature. On the other hand, as described by McClatchie et al. in U.S. Pat. No. 4,103,174, the infrared source can be stabilized against temperature variations by using a radiation loading scheme in combination with a selected source environmental temperature sensitivity without using a temperature controller to maintain the ambient conditions constant. In accordance with the radiation loading scheme of McClatchie et al., the temperature of the infrared source may be maintained relatively constant by providing an infrared radiator which has as high an emissivity as possible and a structure in view of the source which also has a high emissivity so as to prevent reflection back to the source. Since the radiation loading scheme of McClatchie et al. tends to provide a background temperature insensitive to the infrared source, the device of McClatchie et al. may maintain the temperature of the source relatively constant without special heaters or temperature controllers. However, as would be apparent to those skilled in the art, McClatchie et al. maintain the temperature of the infrared source relatively constant by controlling the mounting of the source rather than designing a source which is itself relatively insensitive to ambient conditions.

Other techniques have been taught for providing infrared sources with relatively constant outputs for varying ambient conditions. For example, Brown teaches in U.S. Pat. No. 3,394,259 that a regulator may be used in conjunction with the infrared reference source to control the current to the infrared source and hence the temperature and amount of emitted radiation by disposing a thermistor within the winding of the infrared source. In particular, the thermistor is located within the heater wire and the measured temperature is fed back to a regulator which, in turn, regulates the flow of current to the heater in accordance with variations in the detected temperature, thereby maintaining the emitted infrared energy at a relatively constant temperature level. Brown teaches that best results are achieved when the wire wound body has an emissivity as close to unity as possible. However, although relatively stable, the infrared source of Brown is relatively large and fragile and is thus unsuitable for use as the infrared source in infrared capnographs of the type described in the aforementioned patent applications. Moreover, the temperature detection by the device of Brown is not very accurate since the thermistor can only detect the local temperature at a particular point on a coil which is suspended in air and thus has widely varying temperatures throughout its length.

Accordingly, the present inventors have set out to provide an infrared source which is highly stable, very efficient and very small so that it can fit within a sensor package that is small, lightweight and safe. Preferably, the infrared source temperature may be maintained under servo control and is efficient, easy to manufacture, small in size and rugged. The present invention has been designed to meet these needs.

SUMMARY OF THE INVENTION

The present invention relates to an infrared source which has an output energy density which is maintained substantially constant by adjusting the input power to the infrared heating element in response to a temperature detected by a temperature detecting element disposed in close proximity to the infrared heating element. The design of the infrared source of the invention allows the infrared source to be small, yet highly stable and efficient so that it can be used in infrared detection systems of the type described in the aforementioned patent applications. Preferably, the design of the infrared source of the invention incorporates a platinum resistance temperature detector (RTD) integrated with the heating element so as to provide a means of electronics servo control of the heater temperature. The heating element and the RTD are preferably tightly coupled thermally so as to provide accurate, continuous tracking and control of the heater temperature. The design of the invention provides an infrared energy output of approximately 0.5 μwatts per micron bandwidth at a 4 micron wavelength with less than 1 watt input power to the heating element.

A preferred embodiment of the present invention relates to an infrared source comprising a heating element which emits infrared energy when power is applied thereto, a resistance temperature detector which is electrically isolated from but thermally coupled to the heating element so as to continuously detect the average temperature of the heating element, and a regulator responsive to a temperature detection output of the resistance temperature detector for regulating the power applied to the heating element so as to maintain the infrared energy emitted by the heating element at a desired level. Preferably, the heating element comprises a heater wire and is disposed with respect to the RTD in any of a variety of ways which permits the heater wire and RTD to be tightly thermally coupled.

For example, in a presently preferred embodiment, the infrared source further comprises a ceramic rod about which the heater wire is wound near a tip thereof. In such an embodiment, the ceramic rod acts as a support and heat insulator for the heater wire for thermally insulating the heater wire from the supporting structure of the infrared source. Preferably, the ceramic rod has at least one internal bore in which the resistance temperature detector is concentrically disposed under the heater wire so as to be in close proximity with the heater wire. In a preferred embodiment, the heater wire and resistance temperature detector are threaded through respective internal bores of the ceramic rod from a base of the ceramic rod to the tip thereof. In another embodiment, the heater wire may be instead connected to leads external to the ceramic rod. In either embodiment, the resulting source structure is preferably coated with a glass coating which provides a surface with a desirable emissivity for emission of infrared energy as well as a layer for protecting the heater wire from oxidation. The glass coating also eliminates the burn off (curing) cycle normally required with prior art bare wire heaters.

In an alternative embodiment, the resistance temperature detector comprises a platinum coil which is wound with the heater wire about the ceramic rod. As in the aforementioned embodiment, the heater wire, platinum coil and ceramic rod may be covered by a glass coating so as to provide a surface with a desirable emissivity for emission of the infrared energy as well as a layer for protecting the heater wire from oxidation.

Each embodiment of the present invention may also include a heat insulating plastic housing disposed about a base of the ceramic rod and an elliptical reflector in contact with the plastic housing. Preferably such an elliptical reflector is disposed with respect to the heating element so as to focus infrared energy emitted from the heating element towards a detection point as if the infrared source were a point source.

BRIEF DESCRIPTION OF THE DRAWINGS

The above and other objects and advantages of the invention will become more apparent and more readily appreciated from the following detailed description of the presently preferred exemplary embodiments of the invention taken in conjunction with the accompanying drawings, of which:

FIG. 3 illustrates in more detail a preferred embodiment of an infrared source in accordance with the invention.

FIGS. 4(a) and 4(b) illustrate an alternative embodiment of an infrared source in accordance with the invention.

FIG. 5 illustrates another alternative embodiment of an infrared source in accordance with the invention.

DETAILED DESCRIPTION OF THE PREFERRED EMBODIMENTS

Preferred embodiments of the invention will now be described with reference to FIGS. 2-5. It will be appreciated by those of ordinary skill in the art that the description given herein with respect to those FIGURES is for exemplary purposes only and is not intended in any way to limit the scope of the invention. All questions regarding the scope of the invention may be resolved by referring to the appended claims.

Figure 1:
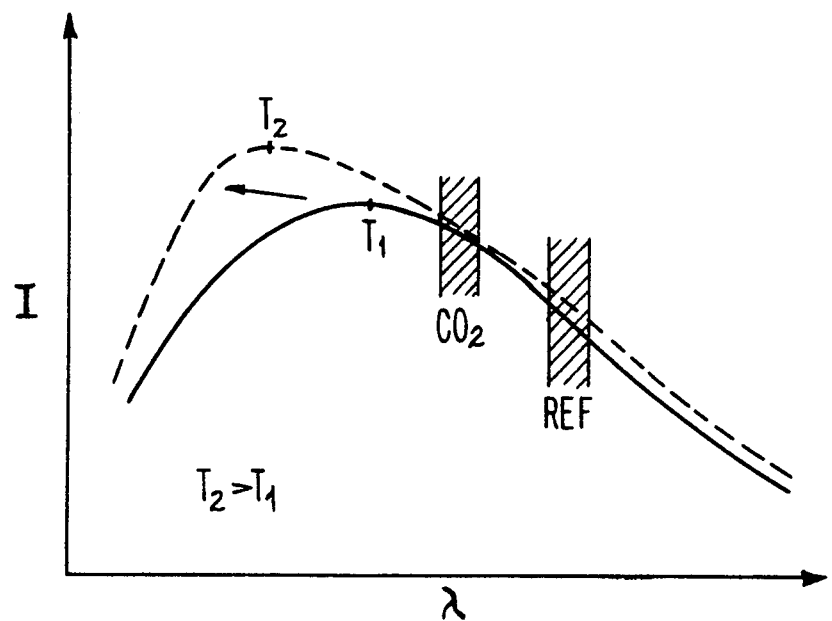
FIG. 1 illustrates the effects on differential absorption of temperature drift and subsequent shift in emission spectra of an infrared source.
Figure 2:
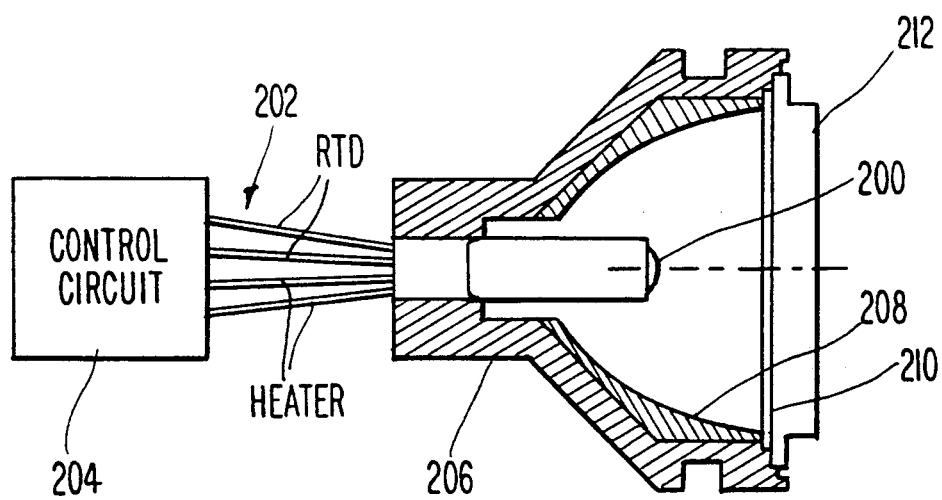
FIG. 2 illustrates a cross-section of a generalized embodiment of an infrared source in accordance with the invention.

FIG. 2 illustrates a generalized embodiment of an infrared source in accordance with the invention. As illustrated, the infrared source of the invention comprises an infrared heating element 200 which, as will be described below with respect to FIGS. 3-5, contains a resistance temperature detector (RTD) disposed within a ceramic rod (FIGS. 3 and 4) or wrapped around the ceramic rod along with the heating wire (FIG. 5). In addition, the infrared heating element 200 so configured is coated with a glass layer to prevent oxidation of the heater wire while also providing a surface with good emissivity.

As shown in FIG. 2, leads 202 from the infrared heating element 200 (and its RTD) are preferably input into a control circuit 204 which controls the power applied to the infrared heating element 200 in accordance with the temperature detected by the RTD. For example, control circuit 204 may contain a bridge circuit of the type described by Brown in U.S. Pat. No. 3,394,259, whereby an imbalance in the bridge circuit caused by the RTD output causes the current applied to the infrared heating element 200 to be varied. Such techniques are believed to be well within the level of skill of those skilled in the art, and accordingly, control circuit 204 will not be described in more detail herein.

Preferably, the infrared heating element 200 of the invention is held in place by a high temperature housing 206 as shown. Such a housing 206 is preferably a plastic insulator which can withstand high temperatures, such as an Envex ™ polyimide. The housing 206 minimizes heat transfer from the infrared source to the outside sensor housing and may be used to hold the infrared heating element 200 in place with respect to a curved reflector insert 208, which, as known by those skilled in the art, focuses the output of the infrared heating element 200 through source aperture 210 and infrared transmitting window 212 towards the target. Such reflector inserts 208 are generally known and are described, for example, by Blunck et al. in U.S. Pat. No. 3,949,231, as being useful in focusing the output energy of the infrared heating element 200. A single mounting point for the infrared heating element 200 with respect to the reflector insert 208 was chosen to facilitate mounting and also to minimize heat conduction paths. Preferably, the tip of the infrared heating element 200 is located optimally within the reflector insert 208 so as to focus the output infrared energy towards the target. In other words, the optical design preferably allows the infrared heating element 200 to approximate a point source within the reflector insert 208.

FIG. 3 illustrates a preferred embodiment of the infrared heating element 200 of the infrared source of the invention in more detail As shown, the infrared heating element 200 preferably comprises a hollow ceramic body 300 which has an RTD coil 302 disposed inside bores 304 near the tip of the ceramic body 300. RTD coil 302 may comprise, for example, a 0.0007" diameter platinum coil with the desired resistance value. Heater coil 306 is then preferably bifilar wound around the outside diameter of the ceramic body 300 about the RTD coil 302. Heater coil 306 preferably comprises a very thin 0.002" diameter Kanthal ™ wire. The wires of the RTD coil 302 and heater coil 306 are preferably threaded through bores 304 as shown and resistance welded at 308 to solderable wires 202, which are preferably of a Palladium alloy. Each wire 202 is preferably strain relieved within the four through holes 304 inside the ceramic body 300 with molten glass 310, which preferably encapsulates the entire body of the infrared heating element 200. Preferably, the coating thickness is on the order of 2 to 5 mils. for ruggedness and protection from oxidation. This implementation is desirable since it also enables the infrared source of the invention to approximate a point source and to have a very fast response time by virtue of the close thermal coupling of the heater 306 and RTD element 302 and because of its small size.

FIGS. 4(a) and 4(b) illustrate another embodiment of the infrared heating element 200 of the invention. As in the embodiment of FIG. 3, the heater wire of heater 306 is preferably concentrated in a small area near the tip of the ceramic rod 300 so that the remainder of the ceramic rod 300 may act as a heat insulator to the insulator mounting base 400. As shown in FIG. 4(b), which is taken along the section lines A—A of FIG. 4(a), inside the ceramic rod 300 concentrically located under the heater wire 306 is RTD element 302, which may be part number SD1 PT100-8A available from Sensing Devices, Inc. As in the embodiment of FIG. 3, the heater wire of heater 306 and the RTD element 302 are in close proximity with each other. Also, as shown, heater 306, ceramic rod 300 and RTD element 302 are preferably coated with molten glass 310 for ruggedness and protection from oxidation. However, unlike FIG. 3, the embodiment of FIG. 4 includes solderable leads 402 to which the terminations of the heater wires of heater 306 are welded before the molten glass coating 310 is applied. As in the embodiment of FIG. 3, this arrangement provides close thermal coupling of the heater 306 and RTD element 302 and allows a very small point source to be formed.

For maximum efficiency in the preferred embodiments, the infrared heating element 200 of the infrared source of the invention is designed to be small in order to provide a very high operating temperature for a given input power. The heater coil 306 and the RTD coil 302 are also preferably concentrically wound near the tip of the hollow ceramic body 300 to minimize heat conduction to the base of housing 206 or insulator mounting base 400. Such an arrangement also enhances the response time of the heater 306. The base of the ceramic body 300 preferably has the four solderable wire terminals 308 which are strain relieved to the ceramic body as previously described. The base may also be supported by a heat insulating plastic (Envex ™) housing 206 as shown in FIG. 2. The entire exterior of the integrated heater/RTD element is also preferably glass coated by glass layer 310 as described to prevent oxidation of the heater wire while providing a surface with very good emissivity. The resulting infrared source is very simple and rugged so that it can withstand a lot of mechanical shock and handling. This is extremely important for use with sensors that are likely to be repeatedly dropped.

FIG. 5 illustrates another alternative embodiment of the invention in which the RTD element 302 within the hollow ceramic body 300 is replaced by an RTD element 500 which is bifilar wound about the ceramic body 300 along with the heater wire of heater 306. As in the embodiments of FIGS. 3 and 4, the heater 306, ceramic body 300 and RTD element 500 are also preferably coated with molten glass 310 for ruggedness and protection from oxidation. In such an embodiment, RTD element 500 can readily measure the average temperature of the heater wire along its entire length. However, this embodiment has proven to be more difficult to manufacture than the embodiments of FIGS. 3 and 4; therefore, the embodiments of FIGS. 3 and 4 are presently preferred.

Not only is the design of the present invention much more rugged and mechanically stable compared to a floating formed coil of the type taught by Brown, for example, but also the present invention may achieve a much higher operating temperature due to the materials used——ceramic, metal and glass. Unlike the source of Brown, hot spots or cold spots in the heater 306 are eliminated by design due to the coil winding method and the glass coating. Moreover, the glass coating 310 over the heater 306 also provides a homogenous radiating surface with good emissivity. Furthermore, the glass and ceramic construction of the preferred embodiment provides the possibility of a simple glass to metal hermetic seal for applications where a back fill gas such as argon is required.

Of course, other temperature detecting elements may be used in place of RTD element 302 or 500. However, the platinum wire RTD element 302, 500 selected in accordance with the present invention is preferred since it is inherently more stable than a thermistor or thermocouple and will provide a typical stability of within 0.1° C. per year. Moreover, the implementation of RTD 302, 500 in the design of the present invention provides a measure of the average temperature of the entire infrared source tip as compared to a localized temperature reading which would result if a thermistor or thermocouple were instead used. Preferably, RTD element 302, 500 has a resistance on the order of 50, ohms +/−1% at 0° C. and has a stability of at least +/−0.3° C. drift in one year. Also, the heater 306 preferably has a resistance on the order of 50 ohms +/−1% for a device which has an operating temperature range between 0 and 550° C.

Since the RTD element 302, 500 and the heater 306 are tightly coupled thermally, the system of the present invention when used with a low drift electronic servo control for the heater temperature will provide a highly stable and repeatable black body curve. In accordance with such an arrangement, the infrared source of the invention also will reach its operating temperature instantly and maintain excellent temperature control even with variations of the ambient temperature. Moreover, the design of the invention provides an infrared energy output of approximately 0.5 µwatts per micron bandwidth at a 4 micron wavelength with less than 1 watt input power to the heating element. Furthermore, the design of the invention also eliminates the lengthy burn off (curing) cycle typically required by bare wire nichrome alloy type heaters of the prior art in order to achieve a high immunity oxide layer. Also, because of the glass protective layer, the infrared source of the invention will maintain a constant emissivity surface throughout its life.

Those skilled in the art will readily appreciate that many modifications to the invention are possible within the scope of the invention. For example, the emission spectrum of the infrared source and the supporting circuitry for the invention may be defined during initial instrument calibration and stored in a calibration memory that stays with the detector when the source of the invention is used with detectors of the type described in the aforementioned patent applications. Accordingly, the scope of the invention is not intended to be limited by the preferred embodiments described above, but only by the appended claims.

We claim:

1. An infrared energy source, comprising:

a heater element which emits infrared energy when power is applied thereto;

a resistance temperature detector which is electrically isolated from but thermally coupled to said heater element so as to continuously detect the average temperature of said heater element; and a regulator responsive to a temperature detection output of said resistance temperature detector for regulating the power applied to said heater element so as to maintain the infrared energy emitted by said heater element at a desired level.

2. An infrared energy source as in claim 1, wherein said heater element comprises a heater wire.

3. An infrared energy source as in claim 2, further comprising a ceramic rod about which said heater wire is wound near a tip thereof, said ceramic rod acting as a support for said heater wire.

4. An infrared energy source as in claim 3, wherein said ceramic rod has at least one internal bore in which said resistance temperature detector is concentrically disposed under said heater wire so as to be in close proximity with said heater wire.

5. An infrared energy source as in claim 4, wherein said heater wire and resistance temperature detector are threaded through respective internal bores of said ceramic rod from a base of said ceramic rod to said tip of said ceramic rod.

6. An infrared energy source as in claim 5, further comprising a protective glass coating about said heater wire, ceramic rod and resistance temperature detector.

7. An infrared energy source as in claim 4, wherein said resistance temperature detector is threaded through said at least one internal bore of said ceramic rod from a base of said ceramic rod to said tip of said ceramic rod and said heater wire is connected to leads external to said ceramic rod.

8. An infrared energy source as in claim 7, further comprising a protective glass coating about said heater wire, ceramic rod and resistance temperature detector.

9. An infrared energy source as in claim 3, wherein said resistance temperature detector comprises a platinum coil which is wound with said heater wire about said ceramic rod.

10. An infrared energy source as in claim 9, further comprising a protective glass coating abut said heater wire, platinum coil and ceramic rod.

11. An infrared energy source as in claim 3, further comprising a heat insulating plastic housing disposed about a base of said ceramic rod and an elliptical reflector in contact with said plastic housing and disposed with respect to said heating element so as to focus infrared energy emitted from said heating element towards a detection point.

* * * * *